United States Patent [19]

Holmquist et al.

[11] Patent Number: 4,908,187

[45] Date of Patent: Mar. 13, 1990

[54] DEVICE FOR DILUTING AND MIXING LIQUIDS AND APPLICATIONS FOR KINETIC ANALYSIS

[75] Inventors: Barton Holmquist, Waltham, Mass.; Robert K. Scopes, Hurstbridge, Australia

[73] Assignee: Endowment for Research in Human Biology, Inc., Boston, Mass.

[21] Appl. No.: 228,786

[22] Filed: Aug. 4, 1988

Related U.S. Application Data

[63] Continuation of Ser. No. 32,546, Apr. 1, 1987, abandoned.

[51] Int. Cl.[4] ............................................. G01N 33/00
[52] U.S. Cl. ................................... 422/81; 73/864.12; 422/100
[58] Field of Search ................. 73/864.12; 422/63–67, 422/68, 100, 80, 81, 102, 116, 133, 224; 436/179, 52

[56] References Cited

U.S. PATENT DOCUMENTS

| | | | |
|---|---|---|---|
| 3,488,154 | 1/1970 | Hronas | 422/81 |
| 3,524,366 | 8/1970 | Hrdina | 422/82 |
| 3,913,790 | 10/1975 | Seidel | 422/100 |
| 4,204,977 | 5/1980 | Zwirlein | 422/133 |
| 4,242,306 | 12/1980 | Kreuer | 422/133 |
| 4,361,407 | 11/1982 | Pellegrini | 422/224 |
| 4,366,119 | 12/1982 | Takeuchi et al. | 422/67 |

Primary Examiner—Michael S. Marcus
Attorney, Agent, or Firm—Allegretti & Witcoff, Ltd.

[57] ABSTRACT

This invention relates to a diluting and mixing device which is capable of diluting a first solution to produce a second solution which is mixed with an undiluted third solution, to reproducibly produce a unique series of combined solutions. Each solution in said series of combined solutions may vary only in the concentration of a single (selected) reactant, and typically, each successive solution becomes increasingly more concentrated in the selected reactant. By employing a modification in procedure, each successive solution in said series may become decreasingly less concentrated in the selected reactant.

This invention further relates to an automated system comprising the device connected to a stepping motor so as to rapidly and reproducibly produce said series of solutions, said device being further connected to an analyzer means for obtaining chemical, biochemical, or physical chemical data on said series of solutions. This invention especially relates to an embodiment of the device for obtaining kinetic data on enzyme reactions in solutions.

The device is useful because it provides a means for rapidly obtaining chemical, biochemical, or physical chemical data on reactions in solution.

9 Claims, 2 Drawing Sheets

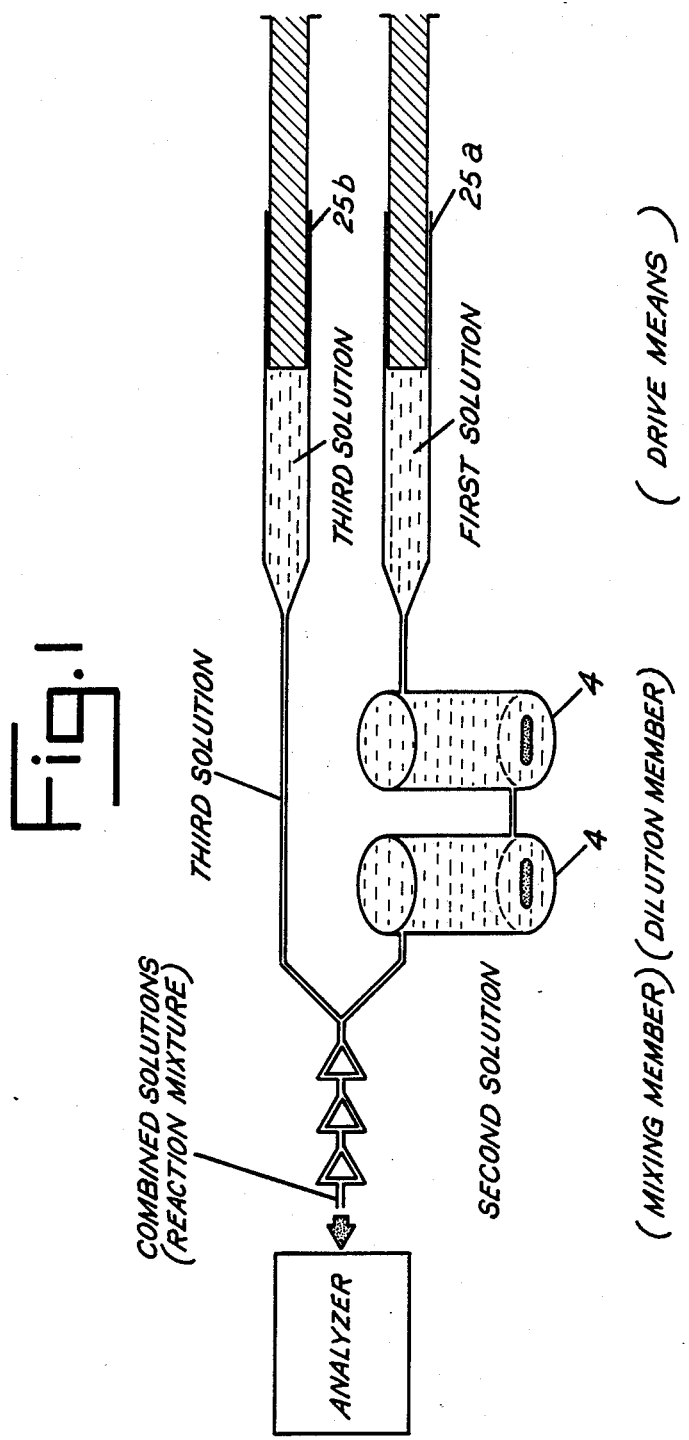

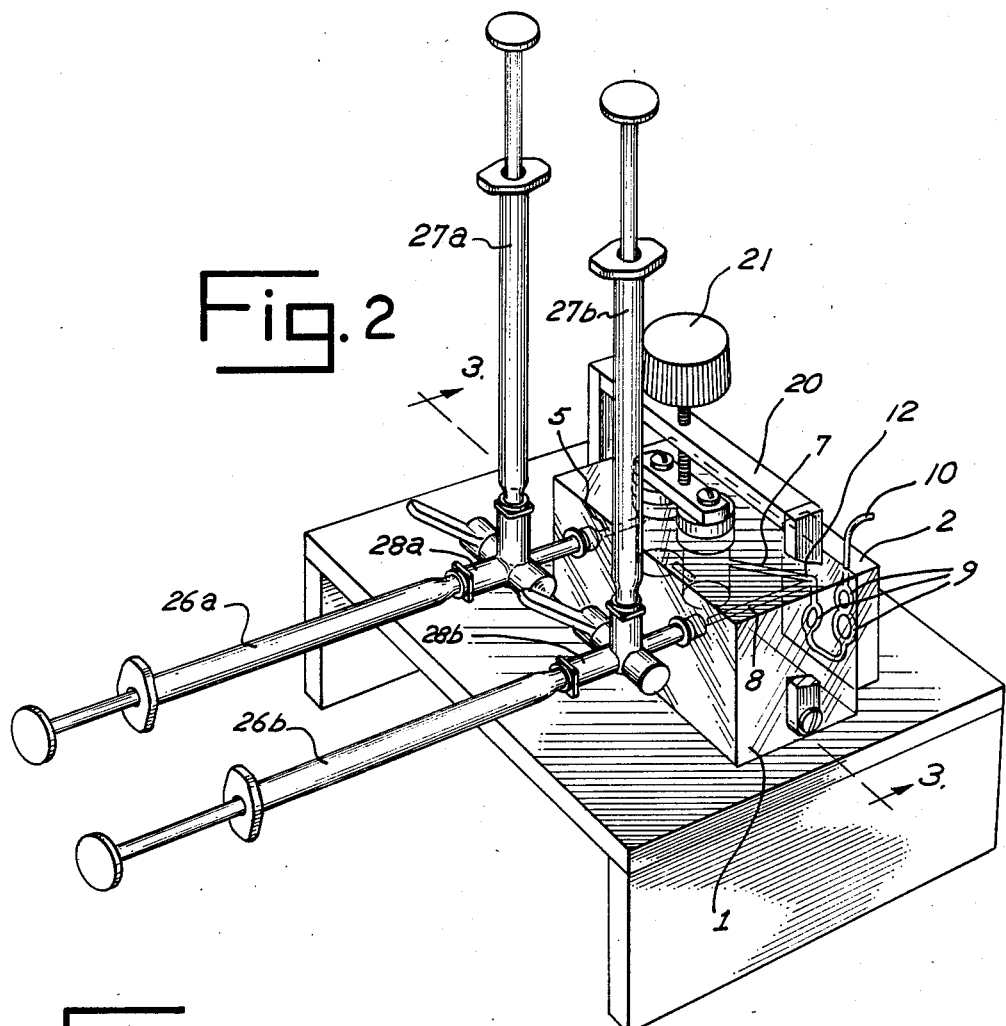
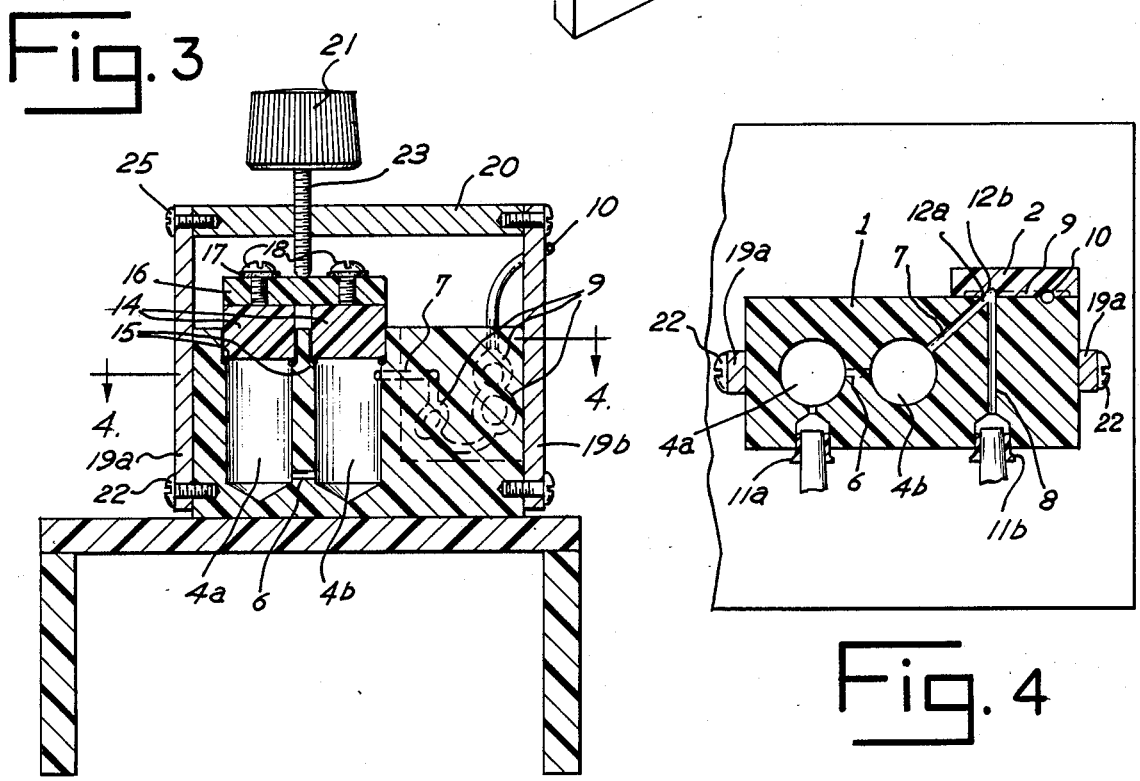

DEVICE FOR DILUTING AND MIXING LIQUIDS AND APPLICATIONS FOR KINETIC ANALYSIS

This application is a continuation of U.S. patent application Ser. No. 07/032546, filed 04/01/87, now abandoned.

BACKGROUND OF THE INVENTION

1. Field of the Invention

This invention relates to a device that quickly, accurately and reproducibly dilutes and mixes two or more solutions to provide incremental concentrations that can be analyzed by any appropriate analyzer.

In a preferred embodiment, this invention relates to a device which is capable of reproducibly mixing one reactant, such as an enzyme, with successively increasing concentrations of another (selected) reactant, so as to produce a series of reacting solutions varying only in the concentration of the selected reactant. The series of reacting solutions so produced can then be monitored to obtain kinetic data on the reaction. The invention further relates to an automated system comprising: the device connected to a stepping motor so as to rapidly produce a series of solutions varying only in the concentration of the selected reactant. The device can be optionally connected to a diode array spectrophotometer capable of simultaneously measuring the rate of reaction at one wavelength and the initial concentration of the selected reactant at another wavelength.

The device is useful because it provides a means for rapidly, accurately and reproducibly obtaining data on chemical, biochemical, and physical chemical reactions in solution.

2. Description of Related Art

The characterization of an enzyme by its Michaelis-Menten constant ($K_m$), its turnover rate ($V_{max}$) and its affinity constant ($K_a$) for activator and inhibitors is a labor intensive and tedious process. It typically requires the initial preparation of two or more master solutions. One of the master solutions, containing the selected reactant, is manually diluted down to produce a series of solutions varying in the concentration of the selected reactant. The appropriate solutions are then manually combined, mixed and introduced into a spectrophotometer to obtain a series of raw data from which the constants can be calculated. The preparation of the multiple dilutions, the manual combining and mixing of solutions, and the subsequent introduction of the combined solutions into a spectrophotometer is not only laborious but the number of manual steps involved makes the process subject to error as well.

It is the object of the present invention to provide a device capable of diluting a selected reactant and of combining and mixing the selected reactant with one or more reactants; said device being connected to a means for introducing the combined solution into an analyzer, such as a spectrophotometer, for monitoring and/or analysis. The overall invention thereby saving both time and labor.

Included among the prior art mixing devices are the gradient producing devices employed in high pressure liquid chromatography. Such devices produce a continually changing solution of eluent by mixing two solvents whereby the percent concentration of both solvents is slowly and gradually changed over time.

The present invention differs from the prior art gradient device in that the present invention is not directed toward gradually producing minute changes in the preparation of both solvents over time. Rather, the present invention is directed toward rapidly producing significant incremental changes in the concentration of a single selected reactant while keeping the concentrations of all other reactants constant.

The prior art mixing of an enzyme solution with its substrate includes devices which gently bubble a gas through a solution into which enzyme and/or substrate solutions have been added. An additional prior art mixing device teaches the mixing of a converged stream of flowing enzyme and substrate by causing the converged stream to flow in a long coil along a horizontal axis wherein segments of the flowing stream are separated from another by the insertion of a gas bubble. In this latter system, mixing is primarily accomplished by employing two solutions of different densities wherein gravity pulls the more dense solution towards the bottom of a flowing stream which is continuously inverted as it passes through the horizontally axised coils.

Unlike the prior art, the present invention accomplishes the mixing of combined and flowing streams of enzyme and substrate by repeatedly diverging and reconverging the flowing streams as they pass through a plurality of diverging and converging fluid passageways. In the present system, mixing occurs as a result of the turbulence created when the divergent streams are repeatedly converged at oblique angles.

The prior art also teaches stopped flow spectrometry, a technique wherein a drive system is used to mix equal volumes of reactants to produce a plurality of solutions of a single unvarying concentration which are propelled into a cell of a spectrophotometer. This prior art device differs from the present invention in that the prior art neither permits the continuous dilution of one of the reactants so as to provide a series of solutions varying only in the concentration of a single reactant nor provides a means for obtaining kinetic data enabling the characterization of an enzyme within a short period of time. Moreover, the prior art does not suggest that such dilutions are possible.

SUMMARY OF THE INVENTION

The present invention relates to a diluting and mixing device which is capable of diluting a first solution to produce a second solution, said second solution being mixed with a third solution to produce a unique series of combined solutions:

wherein each solution in said series of combined solutions optionally varies from all other solutions in said series in the concentration of at least one selected reactant;

and wherein each successive solution in said series optionally becomes either increasingly more concentrated or decreasingly less concentrated in said selected reactant.

The present invention further relates to an automated system comprising the device connected to a stepping motor so as to rapidly and reproducibly produce said series of solutions, said device being further connected to a suitable analyzer for obtaining chemical, biochemical, or physical chemical data on said series of solutions.

The present invention also relates to an embodiment of said diluting and mixing device for use in obtaining chemical and physical chemical data on reactions in solution comprising a fluid driving means, a fluid diluting member, and a fluid mixing member connected in series by a plurality of fluid passageways, said passageways being filled with liquid and forming a closed system such that displacement of a volume of liquid at one end of said system forces the displacement of a substantially equal volume throughout the system;

said fluid driving member acting in a pulselike manner to propel into said dilution means a first solution, and displacing out of said dilution member an equal volume of a second solution containing a selected reactant, which is propelled to the point of its convergence with a like propelled third solution containing an undiluted second reactant, forming a combined solution, said combined solution continuing through said fluid mixing member, and ultimately into an analyzer;

said fluid dilution member for receiving with each pulse of said driving means said first solution and for producing with each pulse a substantially equal volume of a second solution containing said selected reactant, said second solution becoming increasingly more concentrated or decreasingly less concentrated in said selected reactant with each pulse; and said fluid mixing member for mixing said combined solution by providing a plurality of fluid passageways in which said combined solution diverges and reconverges while flowing in response to said driving means to produce a single uniform mixed solution suitable for monitoring and/or analysis.

The present invention further relates to a system encompassing the disclosed device wherein the driving means, preferably a pair of drive syringes, are attached in parallel to a stepping motor, and wherein the exit tube of said mixing member is functionally attached to an analyzer, preferably a spectrophotometer, via a flow cell, such that with each pulse of said stepping motor, a freshly mixed solution of reactants is propelled from the mixing member and into the flow cell, flushing out the old solution preceeding it.

The present invention also encompasses an automated system wherein a computer program controls both the stepping motor and analyzes the data from the spectrophotometer for a preprogramed series of dilutions.

BRIEF DESCRIPTION OF THE DRAWINGS

FIG. 1: Schematic drawing of the diluting and mixing device for diluting a solution A to produce a solution B and for mixing solution B with a solution C to produce a combined solution D (reaction mixture), which is propelled to an analyzer means for monitoring and/or analysis.

FIG. 2: Perspective view of the diluting and mixing device optionally containing two dilution chambers embodied therein.

FIG. 3: Vertical cross-sectional view of the diluting and mixing device.

FIG. 4: Horizontal cross-sectional view of the diluting and mixing device.

BRIEF DESCRIPTION

The basic principle behind the operation of the device for diluting and mixing liquids is diagrammed in FIG. 1, wherein the device is schematically divided into a driving means, a dilution member and a mixing member.

In operation, the device of the present invention mixes a First Solution with a solution or diluent contained in the dilution member to produce a Second Solution. The Second Solution is eventually driven to a point of convergence with a Third solution and the combined solutions are further driven into and out of the mixing member. Upon leaving the mixing member, the combined Second and Third Solutions have become a uniformly mixed Reaction Mixture suited for monitoring or analysis by an analyzer.

By analyzer is meant any device which is capable of analyzing said combined solutions whether electrochemically, thermometrically, fluorimetrically, spectrophotometrically, and the like or whether by nuclear magnetic resonance, electron paramagnetic resonance, circular dichroism and the like.

By producing combined solutions (reaction mixtures) in a stepwise fashion, the diluting and mixing device is capable of producing a unique series of combined solutions wherein each solution in said series of combined solutions may optionally vary from the other solutions in the series in the concentration of at least one selected reactant. Moreover each successive solution in said series of combined solutions can become either increasingly more concentrated or decreasingly less concentrated in the selected reactant depending upon the modification of the procedure employed.

The driving means for the disclosed device preferably consists of two positive displacement devices, such as a pair of syringes, 25a and 25b. It is preferable to employ drive syringes of equal length, although their respective volumes may vary, such that both drive syringes can be easily attached to a single linear drive stepping motor.

Each of the two drive syringes contains its own respective solution within, namely the First Solution and the Third Solution respectively. Displacement within the syringes propels the First and Third Solutions out of the syringes and into the dilution means. Because the mixing, diluting, and driving means form a closed system, the least amount of positive displacement by the syringes propels liquid throughout the system. Accordingly, the volume of liquid propelled into the device equals the volume of liquid propelled out of the device.

Dilution of the First Solution to produce the Second Solution is accomplished by a dilution means comprising 1-4 dilution chambers connected in series. Each dilution chamber is initially filled with a solution or water and reversibly sealed at the top by a sealing means with all air spaces eliminated. Each dilution chamber is further associated with a stirring means, such as a magnetic stirring bar, to insure that each pulse of the freshly introduced concentrated solution is well mixed with diluent before being displaced as a diluted Second Solution by the next injection of a volume of concentrated solution from the drive syringe.

Moreover, in order to insure that only a uniformly diluted Second Solution exits the dilution chamber, it is preferable that the Second Solution exit the columnar dilution chamber at or near the opposite end of the column from where the concentrated First Solution enters—such as top and bottom respectively.

With each consecutive pulse of the drive syringe (25a), the concentrated First Solution from the drive syringe enters the dilution chamber, whereas a more diluted Second Solution exits said chamber. Hence, with each consecutive pulse of the drive syringes, there is a build up of the contents of the First Solution within the dilution chamber. Consequently, the solution within the dilution chamber, which will become the Second Solution, becomes increasingly more concentrated with each pulse.

When only a single 1 ml dilution chamber is employed and when only 0.1 ml of a concentrated First Solution containing the selected reactant is injected into the dilution chamber with each pulse of the driving means, then over the first nine pulses, a series of solutions is produced wherein each successive solution in the series exhibits a somewhat linear increase in the concentration of the selected reactant.

By employing two 1 ml dilution chambers connected in series as in FIG. 1, a series of solutions is produced wherein each successive solution in the series exhibits at first more nearly an exponential increase in the concentration of the selected reactant but becoming more nearly linear as the concentration of the selected reactant in the first dilution chamber approaches the concentration of the selected reactant in the incipient First Solution. Depending upon the number and volume of dilution chambers employed within the device, the device can produce a series of solutions, wherein the concentration of the selected reactant in each solution in the series increases either linearly or exponentially as desired.

It is also within the scope of the present invention to place the highly concentrated solution containing the selected reactant within one or more of the dilution chambers (4) and to substitute water or some other diluent for the First Solution. By employing this embodiment, the device can also produce a series of solutions varying only in the concentration of a single selected reactant. However, unlike the previously discussed embodiment, each successive solution in this series becomes increasingly less concentrated in the selected reactant.

As to the mixing of the converged Second and Third Solutions, the mixing is accomplished by the mixing member which is attached to said dilution member; said mixing member preferrably consists of a plurality of fluid passageways, which diverge and reconverge 1–6 times, preferably 3–4 times while flowing. Upon passing through said passageways, the resulting reconverged solution or Reaction Mixture is uniformly mixed and suitable for monitoring and/or analysis by any suitable analyzer.

In an especially preferred embodiment of the invention, analysis of said series of combined solutions is performed in said analyzer, preferably by way of a flow cell connected in series to the distal end of said mixing member. A pulse (positive displacement) by the pair of driving syringes working in parallel propels sufficient volume of the diluted selected reactant Second Solution and a sufficient volume of another undiluted reactant Third Solution to flush the old reaction mixture out of the flow cell, substituting a freshly mixed reaction mixture containing an increasingly greater concentration of the selected reactant. It is also preferable to employ a micro flow cell (8 ul) so as to reduce the volumes of reactants necessary to cause flushing out of the flow cell. With an 8 ul flow cell,—typically 100 ul of each reactant is sufficient for flushing.

The theoretical concentrations of the selected reactant in each successive reaction mixture varies with each pulse of the driving means. However, the concentration of the selected reactant in each reaction mixture can be calculated by taking into account the selected reactants initial known concentration, the volume of the dilution chamber(s) and the volume of each pulse. Notwithstanding, it is preferable and more accurate to include an internal standard within the concentrated solution containing the selected reactant, such as an indicator dye which absorbs at a non-interferring wavelength. By monitoring the absorbance changes of the indicator dye produced upon each successive dilution, a dilution factor can be calculated and employed to accurately calculate the concentration of the correspondingly diluted selected reactant.

For instance, in a preferred operation of the device, following NAD/NADH coupled enzyme reactions, the selected reactant, whose concentration is to be varied, is a member of the group consisting of an enzyme substrate, an enzyme inhibitor, or an enzyme activator; and the second reactant is the enzyme of interest. When following such NAD/NADH coupled enzyme reactions, it is preferred to use the dye, Rhodamine B as an internal standard, since Rhodamine B has a high molar absorptivity (approximately $10^5 M^{-1} cm^{-1}$) and a sharp absorption peak (552 nm) with virtually no absorbance at the NADH absorption peak (340 nm).

In the NAD/NADH coupled enzyme system discussed above, it is preferable to use a diode array spectrophotometer with the disclosed system so as to monitor the reaction at or near 3 wavelengths: 340 nm, 440 nm, and 552 nm. Readings at or near these wavelengths are recorded every 0.5 sec. over a suitable time period, which is enzyme dependent. For enzymes such as simple dehydrogenases, measurements are made every 0.5 second beginning 2–10 second after injection into the spectrophotometer. The enzyme's rate is calculated from measurements of $A_{340}-A_{440}$ where $A_{340}$ and $A_{440}$ are the absorbances at 340 nm and 440 nm, respectively, whereas the concentration of the selected reactant is calculated from the mean of the measurements of $A_{552}-A_{440}$ where $A_{552}$ and $A_{440}$ are the absorbances at 552 and 440 nm, respectively.

With the disclosed system, a 15 point kinetic run with 15 different substrate concentrations, for example, can be completed in a few minutes.

The within run precision of the device for determining both enzyme rates and substrate concentrations was excellent with the standard deviations ranging between 0.47–1.7% when the $\Delta A$ (difference in absorbance) was 0.05 in 20 seconds.

In an adaptation of the disclosed mixing device, the drive syringes (26a and 26b) are each functionally connected to the dilution block by means of a three-way valve to which a reservoir syringe is also functionally connected (FIG. 2). In this adaption, the reservoir syringes can be used to quickly refill the drive syringe by appropriately turning the three-way valve. In turn, the drive syringes can be functionally reconnected to the dilution block after an appropriate turn of the three-way valve. This adaption provides a rapid means of obtaining a large series of solutions.

In some chemical reactions, especially enzyme reactions, it is preferrable to employ a temperature other than ambient room temperature. Accordingly, in a further adaptation of the disclosed device, the temperature of the solutions within the dilution block may optionally be controlled by contacting said dilution block to a regulatable heat exchanger means in a thermally conductive manner. Typically, the employment of a thermally conductive gel between said dilution block and said heat exchanger increases the efficacy of thermal transmission between said block and said heat exchanger.

The disclosed device can also be used to create a semi-automated system for obtaining chemical or physical chemical data on reactants. In the semi-automated system, the driving means, preferably a pair of drive syringes, are attached in parallel to a stepping motor so as to accurately and reproducibly dispense volumes of reactants, and the exit tube of the mixing means is functionally attached (connected in series) to a flow cell in an analyzer means, such that with each pulse of said stepping motor, a freshly mixed solution of reactants is propelled from the mixing member into the flow cell, flushing out the old solution.

A preferred embodiment of the semi-automated system is employed to obtain kinetic data spectrophotometrically on enzyme systems. In this preferred embodiment, the said flow cell mentioned above is functionally attached to a diode array spectrophotometer, capable of simultaneously monitoring said reaction of interest at one wavelength and said concentration of said selected reactant at a non-interferring wavelength by means of indicator dye in co-solution.

The above disclosed system also can be completely automated by using a computer program to control both the stepping motor and to analyze the data from any interfaceable analyzer for any preprogrammed series of dilutions.

It is a further adaption of the present invention that the First Solution and the solution in the dilution chambers be the same solution. In this instance, the device would accurately and reproducibly produce a series of solutions which would be identical to one another.

Although the device of the present invention has been discussed on a micro scale, it is within the scope of this invention to employ the disclosed dilution and mixing techniques on a macro scale such as in the commercial production of chemical reagents, chemical products, solutions and the like.

DESCRIPTION OF THE PREFERRED EMBODIMENT

The present invention relates to a device for diluting and mixing liquids which is capable of reproducibly mixing one reactant with successively increasing or decreasing concentrations of a selected reactant so as to produce a series of solutions varying only in the concentration of the selected reactant. This device comprises a fluid dilution member, a fluid mixing member, and a fluid drive means and is depicted in FIGS. 2–4.

The fluid dilution member comprises a solid block of non-reactive material, which is preferably machinable and transparent, such as plexiglas, into which are bored a pair of columnar dilution chambers (4) and a plurality of fluid passageways (5–8); said block being called a dilution block (1). The columnar dilution chambers within said dilution block are drilled to a 1.1 cm internal diameter and then they are counterbored at the top to a larger internal diameter, such as 1.27 cm, to provide a lip to hold a correspondingly sized O-ring (15), quad-ring (15) or equivalent. The dilution chambers are then reversibly sealed at the top by a sealing means which seals by compressing said O-ring or quad-ring. The two dilution chambers, namely a first dilution chamber (4a) and a second dilution chamber (4b), each may contain a stirring means within, such as a magnetic stir bar, and are each connected to 1.6 mm diameter fluid passageways, namely a first and second fluid passageway, respectively. The first fluid passageway of each said dilution chamber is for an incipient stream, whereas the second fluid passageway of each said dilution chamber is for an excipient stream. The proximal end of the first dilution chamber's first fluid passageway (5) originates on an outside face of said dilution block and is functionally attached by a connector means (11a) to a fluid drive means (26a), said connector means being affixed to said dilution block. The distal end of said first dilution chamber's first fluid passageway opens into the first dilution chamber. The first dilution chamber's second fluid passageway (6) exits from said first dilution chamber and opens into the second dilution chamber (4b), thereby acting to connect both said dilution chambers in series. The second dilution chamber's second fluid passageway (7) is connected at its proximal end to said second dilution chamber (4b) from where said second fluid passageway is directed towards and converges with an independent fluid passageway (8) at a convergence point (12a), wherein said convergence point is at the distal end of both said passageways and further being at or near an outside face of said dilution block. The proximal end of the independent passageway (8) originates at an outside face of said dilution block, said outside face preferably being directly opposite the outside face associated with said independent fluid passageway's distal end; said proximal end being functionally attached to a driving means, such as a syringe (26b), by a connector means (11b), said connector means being affixed to said dilution block (1). The dilution block further has a relatively flat surface on the outside face associated with said convergence point (12a), said flat surface being suitable for affixation of a mixing member. Preferably, the surface of said dilution block associated with said convergence point is machined to match the appropriate surface of said mixing member. Typically, both said surfaces are vertical surfaces.

The fluid mixing member of the present invention comprises a solid block of non-reactive and preferably transparent material, such as plexiglas, having at least one relatively flat surface into which surface a plurality of channels (9) are cut; said block being called a mixing block (2). The plurality of channels initiate at a point selected (12b) on said flat surface not an edge and diverge and reconverge 1–6 times while extending across said face and end at an edge as a single channel. Preferably a length of the distal end of said channel is sufficiently wider than the preceding channel to accommodate affixation of an exit tube (10) in line with said distal end, said exit tube having substantially the same internal diameter as the preceeding channel (9). The flat surface of mixing block containing the plurality of fluid channels, is affixed in a leakproof manner to the flat surface of the dilution block associated with the convergence point, such that selected point (12b) of said mixing block is superimposed upon point (12a) of said dilution block, said affixation thereby converting said plurality of channels into a plurality of sealed fluid passageways through which converged solutions from fluid passageways (7) and (8) can flow and subsequently mix by diverging and reconverging 1–6 times while flowing therein.

Although the plurality of channels on the face of the mixing block ends on an edge in FIGS. 3–5 and the exit tube (10) is in the same plane as said plurality of channels (9), this is not an essential feature and it is further within the scope of the invention that said plurality of channels may end at other than an edge with an exit tube being other than in the same plane as said plurality of fluid passageways.

The fluid driving means for the present invention are preferably positive displacement devices, such as the syringes (26a) and (26b) depicted in FIGS. 3–5 and the like. The driving means is preferably automated, such as by affixing the butt end of the syringe barrels or pistons to linear drive stepping motor or to a worm drive motor, which can be computer controlled as to both volume dispensed and time before dispensing. When the driving means are syringes, such as (26a) and (26b) said syringes can be functionally connected to the dilution block (1) by luer-type connector means (11a) and (11b) respectively, said connector means being affixed to said dilution block in a substantially leakproof manner. Preferably, between each said connector means (11a) and (11b) and each said respective drive means (26a and 26b), a three-way valve (28a) or (28b) can be connected in series, respectively; said valve further being further connected to its respective reservoir syringe (27a or 27b), which can rapidly refill said respective drive (syringes) means without detachment through said valve (FIG. 2).

The driving means for the present invention acts in a pulsewise manner to propel into said dilution means an undiluted first solution containing a selected reactant, and displacing out of said dilution means an equal volume of the diluted first solution, which is propelled to the point of its convergence with a like propelled solution containing an undiluted second reactant, forming a combined solution, said combined solution continuing with the same pulse through said fluid mixing means, and ultimately into a spectrophotometer for monitoring or analysis. The solution containing the undiluted reactant is preferably propelled by a second drive means in a volume equal to that volume propelled by the first drive means.

The reversible sealing means used to seal the dilution columns (4a) or (4b) comprises the following: two columnar plug type caps (14) as shown in FIGS. 2–4 which are of sufficient diameter to slide downwardly in said dilution chambers and rest their respective bottom surfaces upon said O-rings, quad-rings, or equivalent (15), said columnar caps' bottom surface being slightly convex as to completely displace any air when sealing said chambers; a pressure plate (16) resting upon the top surface of said caps, said pressure plate (16) associated with a pair of small adjustable screwlike devices (18) and a large adjustable screwlike device, said small adjustable screwlike devices threaded through said plate and positioned centrally over each said cap, each said small adjustable screwlike device further associated with a tension means (17); said large adjustable screwlike device (21) threaded through a horizontal member (20) of a three member support assembly, and adjustably positioned over said pressure plate; said support assembly further containing two vertical members (19a) and (19b) pivotally attached near their respective bottom ends to opposite sides of said dilution block by a fastener means (22), and being firmly attached at their respective top ends to opposite ends of said horizontal member by a fastener means (25); whereby when said support assembly is positioned over said pressure plate and said large adjustable screwlike device is adjusted downward, said large adjustable screwlike device contacts the top of said pressure place and coarsely applies a downward pressure on said plate; said plate then applying pressure on said caps; the pressure on said caps being evenly adjusted by said small screwlike devices; said caps then compressing said O-rings so as to form a seal such that when said dilution chambers are pressurized by said drive means, no leakage of solution contained therein occurs.

Alternatively, said reversible sealing means used to seal the dilution chambers (4a) and (4b) could simply be a screw-type cap; the greater columnar diameter of said columnar dilution chambers being threaded in a manner to accept said treaded caps; the threaded caps having a slightly convex bottom surface such that when the threaded caps are screwed downward into a filled dilution chamber, their bottom surface displaces any air and compresses said O-rings (15), quad-rings, or the equivalent, forming a substantially leakproof seal.

The preceding embodiment is given by way of illustration only and in no way should be construed as limiting the invention in spirit or in scope, as many modifications in materials and methods will be apparent from this disclosure to those skilled in the art.

What is claimed is:

1. A device suitable for use in obtaining chemical, biochemical, or physical chemical data on reactions in solution comprising a first and second pulse driven fluid drive means, a fluid dilution member, a fluid mixing member, a control system, and first, second, third, and fourth fluid passageways;
   wherein all said fluid passageways are substantially linear, each said passageway having a single proximal end through which a liquid enters and a single distal end through which a liquid exits;
   said first pulse driven fluid drive means being functionally affixed to the proximal end of said first fluid passageway;
   said fluid dilution member comprising 1 dilution chamber or 2 interconnected dilution chambers, said fluid dilution member having an incipient end and an excipient end, wherein said incipient end of said dilution member is functionally affixed to the distal end of the first fluid passageway and wherein said excipient end of said dilution member is functionally affixed to said proximal end of said second fluid passageway;
   said second pulse driven fluid driven means being functionally affixed to said proximal end of said third fluid passageway;
   said fluid mixing member having an incipient end and an excipient end, said fluid mixing member comprising a fluid passageway diverging and reconverging 1–6 times, said incipient end of said fluid mixing member being functionally affixed to both said distal ends of said second and third fluid passageways respectively, and said excipient end of said fluid mixing member being functionally affixed to said proximal end of said fourth fluid passageway;
   wherein said first and second pulse driven fluid drive means, said first, second, third and fourth fluid passageways, said fluid dilution member and said mixing member form a liquid filled closed system such that displacement of a volume of liquid at one end of the system forces the displacement of a substantially equal volume of liquid at the other end of the system;
   said control system operatively associated with both said first pulse driven fluid drive means and said second pulse driven fluid drive means;
   whereby when said control system associates with both said first pulse driven fluid drive means and said second pulse driven fluid drive means, it causes the displacement (pumping) of a volume of liquid from said first pulse driven fluid drive thereby pumping a volume of a first solution into a substantially larger volume of a transforming solution contained within said fluid diluting member via said first fluid passageway, and causing displacement of an equal volume of said transformed solution from said dilution member to said fluid mixing member, and said second pulse driven fluid drive thereby pumping a volume of a third solution into and through said fluid mixing member via said third fluid passageway, such that both said third solution and said transformed solution converge at or near the incipient end of said mixing member and are mixed during displacement through said mixing member thereby forming a combined homogeneous solution being further displaced by said combined pulses into and out of the distal end of said fourth fluid passageway, said combined homogeneous solution becoming variably less dilute in the components of said first solution with each successive pulse.

2. The device according to claim 1 wherein said mixing member comprises a transparent non-reactant mixing block in which at least one verticle surface is substantially flat, said substantially flat surface having said diverging and reconverging fluid passageway cut into its face; said fluid passageway initiating at a selected point on said flat surface which is not at an edge, a length of the distal end of said fluid passageway being sufficiently wider than the preceding channel to accommodate affixation of an exit tube in line with said distal end; and wherein said mixing block is affixed in an essentially leakproof manner to a substantially flat verticle surface of said dilution member such that said convergence point of said dilution member and said selected point of said mixing block are superimposed upon one another, whereby said affixation converts said open faced diverging and reconverging fluid passageway into a sealed diverging and reconverging fluid passageway in which solutions can be mixed by diverging and reconverging while flowing therethrough.

3. The device according to claim 1 wherein both first pulse driven fluid drive means and said second pulse driven fluid drive means are a positive displacement device driven by a stepping motor.

4. The device according to claim 3 wherein both said positive displacement devices are syringes.

5. The device according to claim 4 wherein both said syringes are driven by a single stepping motor.

6. The device according to claim 2 wherein said substantially flat surface of said mixing block is machined.

7. The device according to claim 1 wherein the excipient end of said mixing member is functionally connected to a flow cell in a spectrophotometer.

8. The device of claim 7 wherein the spectrophotometer is of the diode array type.

9. The device of claim 7 further interfaced to a computer.

* * * * *